United States Patent [19]

Demerson et al.

[11] Patent Number: 4,544,757

[45] Date of Patent: Oct. 1, 1985

[54] PROCESS FOR THE RESOLUTION OF PYRANO[3,4-B]INDOLE-1-ACETIC ACIDS

[75] Inventors: Christopher A. Demerson, Plainsboro; Leslie G. Humber, North Brunswick, both of N.J.

[73] Assignee: American Home Products Corporation, New York, N.Y.

[21] Appl. No.: 580,901

[22] Filed: Feb. 16, 1984

[51] Int. Cl.$^4$ ............................................ C07D 495/04
[52] U.S. Cl. .................................................... 548/432
[58] Field of Search ........................................ 548/432

[56] References Cited

U.S. PATENT DOCUMENTS

| | | | |
|---|---|---|---|
| 3,939,178 | 2/1976 | Demerson et al. | 424/274 |
| 4,100,277 | 7/1978 | Demerson et al. | 548/432 |
| 4,179,503 | 12/1979 | Asselin et al. | 548/432 |

FOREIGN PATENT DOCUMENTS 560219  3/1975  Switzerland .

OTHER PUBLICATIONS

B. Laangstroem et al., Chem. Abst. 91, 193607p (1979) for Chem. Scr., 13, 49 (1979).
P. E. Krieger et al., J. Org. Chem., 43, 4447 (1978).
P. H. Boyle, Quarterly Reviews, 25, 323 (1971).
E. Wehinger et al., Abstr. Papers Am. Chem. Soc. 182 Meet. MEDI 64/1981.
Gerecke, Chem. Abst. vol. 83 (1975) 97294y, Equit Swiss '219.
Demerson et al., Chem. Abst. vol. 99 (1983) 187266a.
Demerson et al., J. Med. Chem. 1983, 26, 1778–1780.
Eliel, Stereochemistry of Carbon Compounds, 1962, pp. 49–53.
Demerson et al., J. Med. Chem. 1975, vol. 18, pp. 189–191.
Maestas et al., Chem. Abst. vol. 85 (1976), 77478z.

*Primary Examiner*—Donald G. Daus
*Assistant Examiner*—Cecilia Shen

[57] ABSTRACT

Mixtures of racemic (±)pyrano[3,4-b]indole-1-acetic acids are resolved with (−)-borneol to obtain the substantially pure (+) and (−)-enantiomers. The resolution involves the formation of a mixture of the diastereoisomeric pyrano[3,4-b]indole-1-acetic acid, (−)-borneol esters, separation of the diastereoisomeric esters, and hydrolysis of the latter esters.

8 Claims, No Drawings

PROCESS FOR THE RESOLUTION OF PYRANO[3,4-B]INDOLE-1-ACETIC ACIDS

BACKGROUND OF THE INVENTION

This invention relates to a process for the resolution of (±)-pyrano-[3,4-b]indole-1-acetic acids to obtain the separate corresponding (+) and (−) optical enantiomers.

The racemic (±)-pyrano[3,4-b]indole-1-acetic acids are well known anti-inflammatory and analgesic agents described by C. A. Demerson et al., U.S. Pat. No. 3,939,178, issued Feb. 17, 1976; C. A. Demerson et al., J. Med. Chem., 18, 189 (1975) and 19, 391 (1976).

The process of this invention involves the condensation of a racemic (±)-pyrano[3,4-b]indole-1-acetic acid with (−)-borneol to obtain a separable diastereoisomeric mixture of the corresponding esters and hydrolyzing the (+) and (−) diastereoisomeric esters. A limited number of esterifications of a racemic acid with an optically active alcohol to give diastereoisomeric esters are described, for example, P. H. Boyle, Quarterly Reviews, 25, 323 (1971). In addition, a few total syntheses of optically active acids using optically active alcohols are described, for example E. Wehinger et al., Abstr. Papers Am. Chem. Soc. 182 Meet. MEDI 64/1981; B. Laangstroem et al., Chem. Abstr. 91, 193607 p (1979) for Chem. Scr., 13, 49 (1979); and P. E. Krieger et al., J. Org. Chem., 43, 4447 (1978).

The above described uses of optically active alcohols are for specific syntheses of various acids in limited quantities. Such use of optically active alcohols are known to be of little importance for the general resolution of racemic acids, see P. H. Boyle, cited above, at p.325. Usually the mixture of diastereoisomeric esters cannot be separated to obtain the individual enantiomers.

The process of this invention resulted from the discovery that a diastereoisomeric mixture of pyrano[3,4-b]indole-1-acetic acid (−)-borneol esters can be easily separated. This process gives individual (+) and (−)-enantiomers of a pyrano[3,4-b]indole-1-acetic acid in a commerically feasible operation and in high yield.

SUMMARY OF THE INVENTION

The process of this invention comprises:

(a) esterifying a racemic (±)pyrano[3,4-b]indole-1-acetic acid of formula I

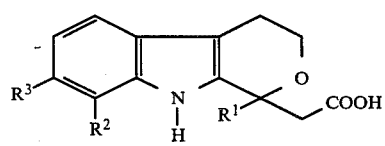

in which $R^1$ is lower alkyl, and $R^2$ and $R^3$ each is hydrogen, lower alkyl or halo with (−)-borneol to obtain a diastereoisomeric mixture of a corresponding compound of formula II

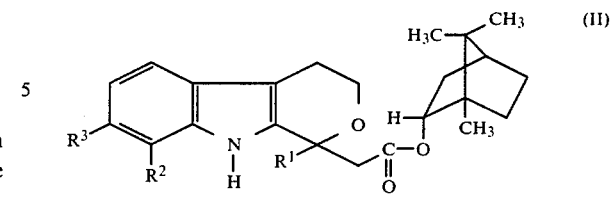

in which $R^1$, $R^2$ and $R^3$ are as defined above;

(b) separating the diastereoisomers;

(c) hydrolyzing the (+) or (−)-diastereoisomer of formula II under alkaline conditions; and (d) isolating the corresponding (+) or (−)-enantiomer of formula I in which $R^1$, $R^2$ and $R^3$ are as defined herein.

In a preferred process, (±)-1,8-diethyl-1,3,4,9-tetrahydropyrano[3,4-b]indole-1-acetic acid is resolved with (−)-borneol to obtain (+)-1,8-diethyl-1,3,4,9-tetrahydropyrano[3,4-b]indole-1-acetic acid.

DETAILED DESCRIPTION OF THE INVENTION

The term "lower alkyl" as used herein means straight and branched chain alkyl radicals containing from one to five carbon atoms and includes methyl, ethyl, propyl, 1-methylethyl, butyl, 1,1-dimethylethyl and the like, unless stated otherwise.

The term "halo" as used herein means bromo, chloro, fluoro and iodo, unless stated otherwise.

The first step in the process for resolving a racemic compound of formula I in which $R^1$, $R^2$ and $R^3$ are as defined herein involves the esterification of the compound of formula I with (−)-borneol to obtain the diastereoisomeric mixture of the corresponding compound of formula II in which $R^1$, $R^2$ and $R^3$ are as defined herein. A number of the methods known in the art can be utilized for this esterification, for example, use of an acid chloride or bromide of the acid of formula I; acid catalyzed esterification; use of a dehydrating agent, i.e. a dialkylcarbodiimide; and use of a dehydrating agent in the presence of an esterification catalyst, i.e. N-hydroxysuccinimide, 2,4,5-trichlorophenol, 1-hydroxybenzotriazole and 4-dimethylaminopyridine. In the preferred method of esterification, the racemic compound of formula I is condensed with about 1.0 to 1.5 molar equivalents of (−)-borneol in the presence of about 1.0 to 1.5 molar equivalents of N,N'-dicyclohexylcarbodiimide and about 0.1 to 0.15 molar equivalents of 4-dimethylaminepyridine in an inert organic solvent, for example, diethyl ether, diisopropyl ether, chloroform or dimethylformamide. The condensation reaction is allowed to proceed at about 15° to 30° C. for about 10 to 30 hours. After a standard work-up, a diastereoisomeric mixture of the corresponding compounds of formula II are obtained. The diastereoisomeric mixture can be separated to obtain the individual diastereoisomers by using chromatography on a silica gel adsorbant with a suitable eluant. The chromatography can be conducted by using a thin layer of adsorbant on plates, a column of adsorbant at atmospheric pressure or a column of adsorbant under high pressure. A preferred eluant for the chromatography is about 3 to 10 percent ethyl acetate in hexane.

Each of the separated diastereoisomers of formula II is hydrolyzed under alkaline conditions to obtain the corresponding (+) or (−) enantiomer of formula I in which $R^1$, $R^2$ and $R^3$ are as defined herein. Preferred conditions for the hydrolysis involve reacting the individual diastereoisomers of formula II with an aqueous solution of about two to five molar equivalents of an alkali hydroxide or carbonate, preferably sodium or potassium hydroxide, and a water miscible organic solvent, preferably methanol or ethanol at about 60° to 80° C. for one to ten hours. After hydrolysis is complete, the alkaline solution is acidified, preferably with a dilute mineral acid, and the individual enantiomers of formula I are extracted and purified.

The following examples illustrate further this invention:

EXAMPLE 1

1,8-Diethyl-1,3,4,9-tetrahydropyrano[3,4-b]indole-1-Acetic acid, (−)-borneol Esters A mixture consisting of (±)-1,8-diethyl-1,3,4,9-tetrahydrpyrano[3,4-b]indole-1-acetic acid (100 g, 0.348 mol), (−)-borneol (64.46 g, 0.418 mol), 4-dimethylaminopyridine (5.09 g, 0.0417 mol) and N,N'-dicyclohexylcarbodiimide (86.24 g, 0.418 mol) in 1.5 liters of diethyl ether was stirred at 22° C. for 18 hours. The reaction was cooled in an ice-water bath and filtered. The filtrate was washed once with 5% aqueous sodium hydroxide, twice with 5% hydrochloric acid and twice with water. After drying over magnesium sulfate and evaporation of the solvent, 160.3 g of a semisolid was obtained. Filtration through 1.5 kg of silica gel using 10% ethyl acetate in hexane as eluant afforded 119.3 g of the mixture as a solid. Preparative high pressure liquid chromatography (using batches of 20–25 g) using Prepak 500 silica gel cartridges and 3% ethyl acetate in hexane as eluant separated the (+) and (−) esters of the title compound. Evaporation of the appropriate eluates gave 52.33 g of the (+)-diastereoisomer: mp 142°–143° C.; $[\alpha]_D +47.4°$ (1% in ethanol); and Anal. Calcd for $C_{27}H_{37}NO_3$: C, 76.56% H, 8.81% N, 3.31% and Found: C, 76.60% H, 8.71% N, 3.28%. The (−)-diastereoisomer (53.33 g) had mp 93°–96° C.; $[\alpha]_D -61.4°$ (1% in ethanol); and Anal. Found: C, 76.71% H, 8.72% N, 3.21%.

EXAMPLE 2

Hydrolyses of Borneol Esters

The (−)-diastereoisomeric ester, obtained from Example 1, was dissolved in methanol (1 liter) containing potassium hydroxide (34.8 g) and water (260 ml). The mixture was refluxed while stirring for 3 hr. Most of the methanol was distilled off, water (500 ml) was added and the mixture was extracted with toluene. The aqueous phase was acidified with 6N hydrochloric acid and extracted with chloroform. The chloroform extracts were washed with water, dried and the solvent removed to afford crude (+)-enantiomer (32.5 g) which was purified by chromatography on 1 kg of silica gel impregnated with phosphoric acid by stirring the silica gel with a 1% solution of phosophoric acid in methanol, followed by air drying. Elution with 10% acetone in toluene gave the pure (+)-enantiomer. It was obtained as a solid by dissolving in benzene (100 ml) and pouring into cold petroleum ether (bp 30°–60° C., 1.2 liters) with stirring. Subsequent crystallization from benzene-petroleum ether (bp 30°–60° C.) gave the pure enantiomer, (+)-1,8-diethyl-1,3,4,9-tetrahydropyrano[3,4-b]indole-1-acetic acid (24.02 g): mp 138°–140° C.; $[\alpha]_D +25.2°$ (3% in ethanol); and Anal. Calcd for $C_{17}H_{21}NO_3$: C, 71.05% H, 7.37% N, 4.88% and Found: C, 71.14% H, 7.36% N, 4.81%. In the same manner, the (+)-diastereoisomeric ester, obtained from Example 1, gave (−)-1,8-diethyl-1,3,4,9-tetrahydropyrano[3,4-b]indole-1-acetic acid (21.46 g): mp 139°–141° C.; $[\alpha]_D -25.6°$ (3% in ethanol); and Anal. Found: C, 71.09% H, 7.37% N, 4.84%.

EXAMPLE 3

Effect on Primary Inflammation of Adjuvant Induced Arthritis

The method used was a modification of that described by J. Wax et al., J. Pharmac. Exp. Ther., 192, 166 (1975). Groups of rats were injected intradermally in the left hindpaw (injected hindpaw) with 0.1 ml of a fine suspension of killed and dried *Mycobacterium butyricum* (Difco) at a concentration of 5 mg/ml in liquid paraffin (Freund's complete adjuvant). Drugs were administered immediately before the adjuvant, 24 h and 48 h after the adjuvant (day 0, 1 and 2). The injected hindpaw volume was measured before the adjuvant and 24 after the last drug administration (day 3). The difference between the hindleg volume before the adjuvant injection and the day 3 reading represented the edema volume. Rats showing an inhibition of hindpaw edema of 25% or more when compared to the mean edema volume of the control group (10 rats) were considered to exhibit an anti-inflammatory effect. The dose which produced a positive effect in half the rats ($ED_{50}$) was calculated by probit analysis. (D. J. Finney, Statistical Method in Biological Assay, MacMillan, New York, 1978). There were 10 to 20 rats per dose and 4 dose levels were used. An adjuvant-injected control group receiving water only was also included. Hindleg volume was determined by a mercury displacement method. Hindlegs were dipped in mercury up to the hairline and the amount displaced was read in grams on a direct reading balance. It represented the volume of the hindleg (13.6 g of mercury=1 ml). Male Charles River albino rats weighing 180 to 200 g were used. The results are expressed as $ED_{50}$'s, the dose which reduces, by 25% the edema of primary adjuvant arthritis in 50% of the rats. In this model the $ED_{50}$ for (+)-1,8-diethyl-1,3,4,9-tetrahydropyrano[3,4-b]indole-1-acetic acid was 0.7±0.3 mg/kg, while the (−)-enantiomer was inactive. The $ED_{50}$ of the (±)-racemate in this test was 1.1±0.5 mg/kg.

We claim:

1. A process for resolving a racemic (±)-compound of formula I

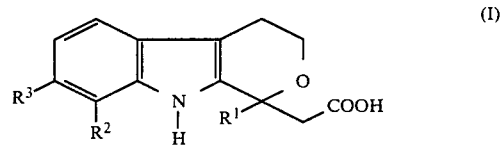

in which $R^1$ is lower alkyl, and $R^2$ and $R^3$ each is hydrogen, lower alkyl or halo to obtain the corresponding (+) or (−)-enantiomer of formula I in which $R^1$, $R^2$ and $R^3$ are as defined herein, which comprises:

(a) esterifying a racemic (±)-compound of formula I in which $R^1$, $R^2$ and $R^3$ are as defined herein with (−)-borneol to obtain a diastereoisomeric mixture of a corresponding compound of formula II

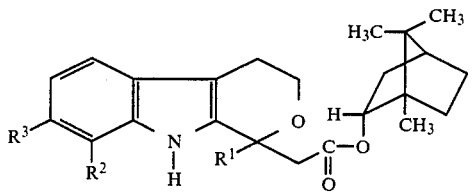

in which $R^1$, $R^2$ and $R^3$ are as defined herein;
(b) separating the diastereoisomers;
(c) hydrolyzing the diastereoisomers of formula II in which $R^1$, $R^2$ and $R^3$ are as defined herein with an aqueous alkaline solution; and
(d) isolating the substantially pure corresponding (+) or (−)-enantiomer of formula I in which $R^1$, $R^2$ and $R^3$ are as defined herein.

2. The process of claim 1 wherein
(a) the racemic (±)-compound of formula I in which $R^1$, $R^2$ and $R^3$ are as defined herein is esterified with (−)-borneol in the presence of N,N′-dicyclohexylcarbodiimide to obtain a diastereoisomeric mixture of a corresponding compound of formula II in which $R^1$, $R^2$ and $R^3$ are as defined herein;
(b) separating the diastereoisomers by chromatography through an adsorbent of silica gel;
(c) hydrolyzing the diastereoisomers of formula II in which $R^1$, $R^2$ and $R^3$ are as defined herein with an aqueous solution of sodium hydroxide or potassium hydroxide; and
(d) acidifying the alkaline hydrolysis solution with a mineral acid and isolating the corresponding (+) or (−)-enantiomer of formula I in which $R^1$, $R^2$ and $R^3$ are as defined herein.

3. The process of claim 2 wherein the esterification of step (a) is conducted in the presence of a catalytic amount of 4-dimethylaminopyridine.

4. A process for resolving racemic (±)-1,8-diethyl-1,3,4,9-tetrahydropyrano[3,4-b]indole-1-acetic acid to obtain (+)-1,8-diethyl-1,3,4,9-tetrahydropyrano[3,4-b]indole-1-acetic acid, which comprises:
(a) esterifying racemic (±)-1,8-diethyl-1,3,4,9-tetrahydropyrano[3,4-b]indole-1-acetic acid with (−)-borneol to obtain a diastereoisomeric mixture of (+) and (−)-1,8-diethyl-1,3,4,9-tetrahydropyrano[3,4-b]indole-1-acetic acid, (−)-borneol ester;

(b) separating the (−)-diastereoisomer;
(c) hydrolyzing the (−)-1,8-diethyl-1,3,4,9-tetrahydropyrano[3,4-b]indole-1-acetic acid, (−)-borneol ester with an aqueous alkaline solution; and
(d) isolating the substantially pure enantiomer (+)-1,8-diethyl-1,3,4,9-tetrahydropyrano[3,4-b]indole-1-acetic acid.

5. The process of claim 4 wherein
(a) the racemic (±)-1,8-diethyl-1,3,4,9-tetrahydropyrano[3,4-b]indole-1-acetic acid is esterified with (−)-borneol in the presence of N,N′-dicyclohexylcarbodiimide to obtain a diastereoisomeric mixture of (+) and (−)-1,8-diethyl-1,3-4,9-tetrahydropyrano[3,4-b]indole-1-acetic acid, (−)-borneol ester;
(b) separating the (−)-diastereoisomer by chromatography through a column of silica gel;
(c) hydrolyzing (−)-1,8-diethyl-1,3,4,9-tetrahydropyrano[3,4-b]indole-1-acetic acid, (−)-borneol ester with an aqueous solution of sodium hydroxide or potassium hydroxide; and
(d) acidifying the alkaline hydrolysis solution with a mineral acid and isolating the substantially pure enantiomer (+)-1,8-diethyl-1,3,4,9-tetrahydropyrano[3,4-b]indole-1-acetic acid.

6. The process of claim 5 wherein the esterification of step (a) is conducted in the presence of a catalytic amount of 4-dimethylaminopyridine and the chromatography in separation step (b) is conducted with an eluant of three to 10 percent of ethyl acetate in hexane.

7. A (+) or (−)-diastereoisomer of a compound of the formula

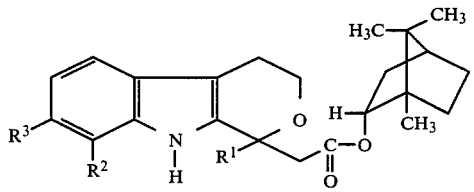

in which $R^1$ is lower alkyl, and $R^2$ and $R^3$ each is hydrogen, lower alkyl or halo.

8. The compound of claim 7, which is (−)-1,8-diethyl-1,3,4,9-tetrahydropyrano[3,4-b]indole-1-acetic acid, (−)-borneol ester.

* * * * *